(12) United States Patent
DiFoggio

(10) Patent No.: US 7,387,021 B2
(45) Date of Patent: Jun. 17, 2008

(54) METHOD AND APPARATUS FOR RESERVOIR CHARACTERIZATION USING PHOTOACOUSTIC SPECTROSCOPY

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 299 days.

(21) Appl. No.: 11/135,802

(22) Filed: May 24, 2005

(65) Prior Publication Data

US 2006/0266108 A1  Nov. 30, 2006

(51) Int. Cl.
  *E21B 47/08* (2006.01)
(52) U.S. Cl. .................................... 73/152.55
(58) Field of Classification Search ........... 73/152.55
  See application file for complete search history.

(56) References Cited

U.S. PATENT DOCUMENTS

| | | | | |
|---|---|---|---|---|
| 4,492,862 | A | 1/1985 | Grynberg et al. | 250/255 |
| 5,942,440 | A * | 8/1999 | Dooley et al. | 436/146 |
| 6,160,255 | A | 12/2000 | Sausa | |
| 6,236,455 | B1 | 5/2001 | Autrey et al. | |
| 6,608,683 | B1 | 8/2003 | Pilgrim et al. | |
| 6,618,148 | B1 | 9/2003 | Pilgrim et al. | |
| 6,662,040 | B1 * | 12/2003 | Henrichs et al. | 600/431 |
| 6,792,354 | B1 | 9/2004 | O'Meara, Jr. | |
| 2001/0022657 | A1 * | 9/2001 | Autrey et al. | 356/432 |
| 2005/0117155 | A1 | 6/2005 | Kosterev et al. | |

OTHER PUBLICATIONS

Foster et al., Laser Photoacoustic Spectroscopy: A Versatile Absorption-Spectroscopic Technique, Feb. 1999, pp. 96S-108S.
Kosterev et al., Trace-Gas Detection In Ambient Air With A Thermoelectrically Cooled, Pulsed, Quantum-Cascade Distributed Feedback Laser, Applied Optics, vol. 39, No. 36, Dec. 2000, pp. 6866-6872.
Tittel et al., Recent Advances Of Trace Gas Sensors Based On Infrared Semiconductor Lasers: Opportunities And Challenges, Rice University, Houston, Texas, Oct. 19, 2001.
Kosterev et al., Cavity Ringdown Spectroscopic Detection Of Nitric Oxide With A Continuous-Wave Quantum-Cascade Laser, Applied Optics, vol. 40, No. 30, Oct. 20, 2001, pp. 5522-5529.
Kosterev et al., Quartz-Enhanced Photoacoustic Spectroscopy, Optic Letters, vol. 27, No. 21, Nov. 1, 2002, pp. 1902-1904.
Photoacoustic Water Vapour Measurement System For Natural Gas Industry, University of Szeged, Photoacoustic Research Group, http://photoacoustics.hu, 5 pages, retrieved Apr. 25, 2005.

(Continued)

*Primary Examiner*—Robert Raevis
(74) *Attorney, Agent, or Firm*—Madan, Mossman & Sriram, P.C.

(57) ABSTRACT

A method and apparatus are provided that assess reservoir compartmentalization by determining whether there are compositional differences such as whether the isotopic ratios of carbon (13C/12C) or of oxygen (17O/18O) are the same or different in various parts of the reservoir. A quartz enhanced photoacoustic spectrometer is provided for analysis of reservoir samples taken in various parts of the reservoir for comparison of geochemical composition to estimate reservoir compartmentalization.

20 Claims, 4 Drawing Sheets

OTHER PUBLICATIONS

Photoacoustic Water Vapour Concentration Measuring System For The Natural Gas Industry, University of Szeged, Photoacoustic Research Group, http://www.photoacoustics.hu, 1 page, retrieved Apr. 25, 2005.

Photoacoustic Hydrogen Sulfide Concentration Measuring System, University of Szeged, Photoacoustic Research Group, http://www.photoacoustics.hu, 1 page, retrieved Apr. 25, 2005.

Assessing Reservoir Compartmentalization Using Oil Geochemistry, www.oiltracers.com, 7 pages, retrieved Apr. 25, 2005.

Reservoir Oil Fingerprinting, www.humble-inc.com/rof_app99-2.htm, 18 pages, retrieved May 3, 2005.

Using Mud Gas Logging (MGL) And Stable Isotope Measurements To Identify Pay Zones, Assess Hydrocarbon Type And Evaluate Reservoir Compartmentalization, http://gaschem.com/mud.html, 3 pages, retrieved May 3, 2005.

Using Gas Geochemistry To Assess Gas Reservoir Compartmentalization, http://www.gaschem.com/assess.html, 4 pages, retrieved May 3, 2005.

Recognizing Reservoir Compartmentalization Increases Production, http://www.pttc.org/solutions/13.htm, 6 pages, retrieved May 3, 2005.

* cited by examiner

METHOD AND APPARATUS FOR RESERVOIR CHARACTERIZATION USING PHOTOACOUSTIC SPECTROSCOPY

BACKGROUND OF THE INVENTION

1. Field of the Invention

The present invention relates to the field of formation fluid sampling and analysis and in particular to the field of reservoir characterization using photoacoustic spectroscopy.

2. Summary of the Related Art

To obtain hydrocarbons such as oil and gas, boreholes are drilled into the earth by rotating a drill bit attached to the end of a drill string. Modern directional drilling systems generally employ a drill string having a bottom hole assembly (BHA) and a drill bit at an end thereof that is rotated by a drill motor (mud motor) and/or by rotating the drill string. A number of downhole devices placed in close proximity to the drill bit measure certain downhole operating parameters associated with the drill string. Such devices typically include sensors for measuring downhole temperature and pressure, azimuth and inclination measuring devices and a resistivity-measuring device to determine the presence of hydrocarbons and water. Additional downhole instruments, known as logging-while-drilling (LWD) tools, are frequently attached to the drill string to determine the formation geology and formation fluid characteristics and conditions during the drilling operations. Analytical sampling devices are also deployed from the wireline into a wellbore after drilling.

Commercial development of hydrocarbon fields requires significant amounts of capital. Before field development begins, operators desire to have as much data as possible regarding the nature of the hydrocarbon formation, in order to evaluate the reservoir for commercial viability. Despite the advances in data acquisition during drilling using the MWD systems and wire line analysis applications, it is often necessary to conduct further testing of the hydrocarbon reservoirs in order to obtain additional data. Therefore, after the well has been drilled, the hydrocarbon zones are often tested with other test equipment such as wire line tools, which are used to further analyze and monitor the formation. Samples are taken from different wells at different locations in the reservoir. These samples are compared to estimate reservoir compartmentalization of the reservoir.

The degree of reservoir compartmentalization is of great commercial importance. Multi-billion dollar decisions on how to develop a reservoir (well location, types of production facilities, etc.) are based on whether or not a reservoir is compartmentalized. Oil producers want to know whether different sections of a reservoir are separate compartments (across which fluids do not flow) or whether they are connected. Separate compartments must be drained separately and may need different types of processing for their fluids. Thus, there is a need for an accurate method and apparatus for determining whether or not a reservoir is compartmentalized.

SUMMARY OF THE INVENTION

The present invention provides a method and apparatus for photoacoustic spectroscopy (PAS) for analysis of reservoir samples to estimate compartmentalization of a reservoir. Generally, the resolution of PAS is only sufficient to distinguish the spectrum of one molecule from the spectrum of another molecule although some researchers have been able to achieve much better resolution with PAS (A. A. Kosterev, R. F. Curl, and F. K. Tittel, Optics Letters, Vol. 24, No. 23, Dec. 1,1999). In one aspect of the invention a method and apparatus are provided for quartz-enhanced photoacoustic spectroscopy (QEPAS) for analysis of formation samples to estimate compartmentalization of the reservoir. The resolution of QEPAS is better than that of PAS (A. A. Kosterev, Yu. A. Bakhirkin, R. F. Curl, and F. K. Tittel, Quartz-enhanced photoacoustic spectroscopy (QEPAS), OPTICS LETTERS, Vol. 27, No. 21, Nov 1, 2002). Therefore, QEPAS can not only distinguish the spectrum of one type of molecule from that of another type of molecule (for example, CO versus $CO_2$) but it can also distinguish the spectra of different isotopes of the same molecule (for example, $^{12}CO_2$ versus $^{13}CO_2$). The method and apparatus of the present invention provide functionality and structure for analyzing a first sample from a first location in the reservoir using a photoacoustic spectrometer (PAS); analyzing a second sample from a second location in the reservoir using the PAS; and comparing the analysis of the first sample to the analysis of the second sample to estimate reservoir compartmentalization.

In another aspect of the invention the PAS further comprises a quartz-enhanced PAS (QEPAS). In another aspect of the invention the analyzing further comprises estimating isotopic ratios for the samples, wherein the isotopic ratios further comprise at least one of the set consisting of isotopic ratios for carbon (13C/12C) or for oxygen (17O/18O). In another aspect of the invention the QEPAS/PAS analysis is performed downhole. In another aspect of the invention the QEPAS/PAS analysis is performed at the surface.

Examples of certain features of the invention have been summarized here rather broadly in order that the detailed description thereof that follows may be better understood and in order that the contributions they represent to the art may be appreciated. There are, of course, additional features of the invention that will be described hereinafter and which will form the subject of the claims appended hereto.

BRIEF DESCRIPTION OF THE DRAWINGS

For detailed understanding of the present invention, references should be made to the following detailed description of the embodiment, taken in conjunction with the accompanying drawings, in which like elements have been given like numerals, wherein.

DETAILED DESCRIPTION OF THE INVENTION

Figure 1:
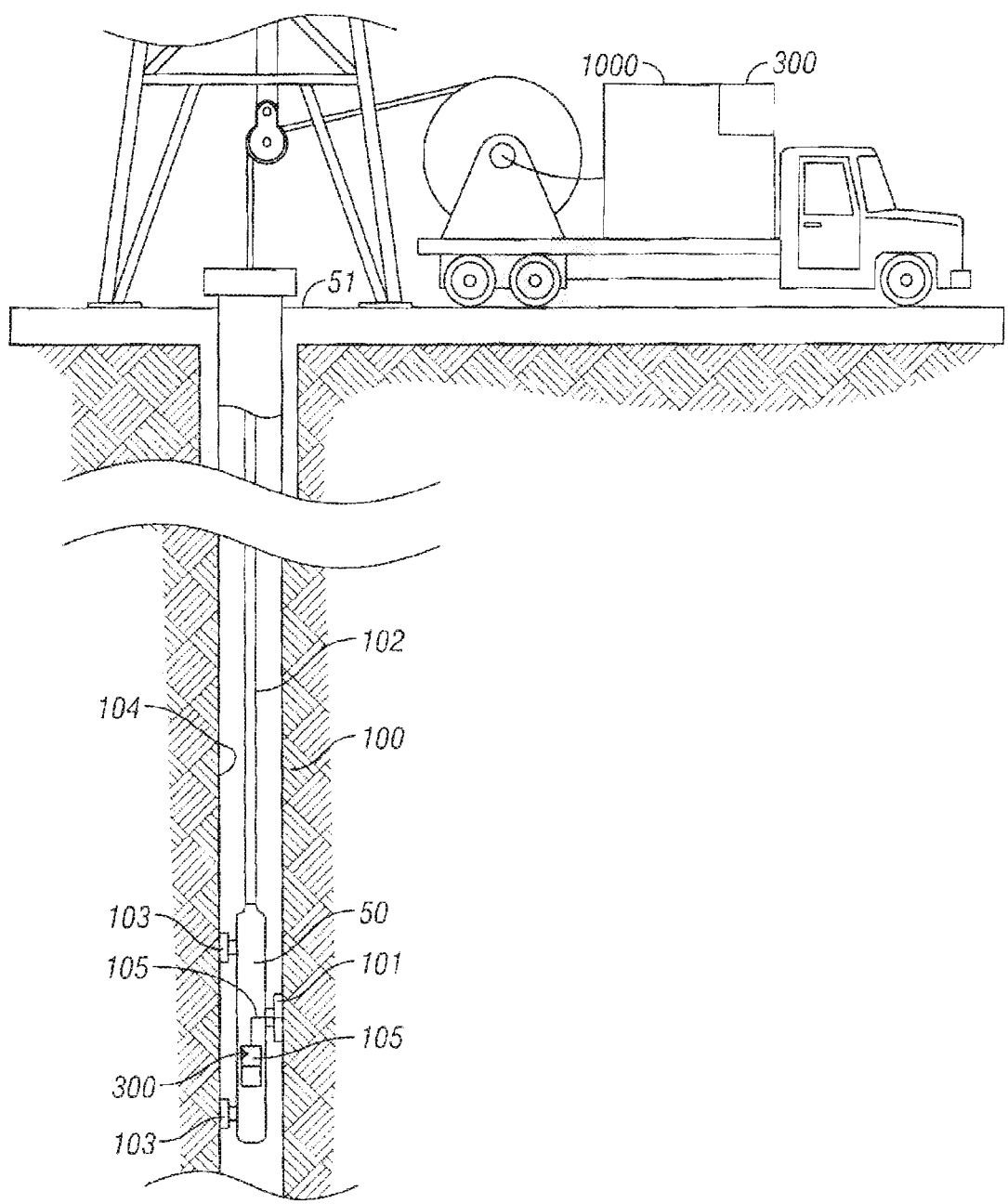
FIG. 1 is an illustration of a plurality of wells and samples taken to estimate reservoir compartmentalization.

The present invention provides a method and apparatus to estimate and assess reservoir compartmentalization by determining whether or not the fluid geochemistry is the same in different parts of the reservoir. For example, it can be used to assess whether the isotopic ratios of carbon (13C/12C) or of oxygen (17O/18O) are the same or different in two or more samples from taken from various parts of the reservoir. These isotopic ratios have typically been measured by a mass spectrometer or gas chromatograph. Recently, there have been developments in using a tunable diode lasers in combination with a traditional light-sensitive detector to analyze reservoir samples. Photoacoustic spectroscopy (PAS) is well known in the art. PAS may use a tunable diode laser in conjunction with an acoustic sensor such as a piezoelectric microphone to detect the sound waves generated when light is absorbed. This approach is different than using a tunable diode laser in conjunction with a light-sensitive detector, such as a photodiode. Thus, PAS is less sensitive to a high downhole temperature which may adversely affect a light sensor such as a photodiode but which has less effect on a PAS piezoelectric microphone. Repeating pulses of laser light (corresponding to the absorption wavelength of a particular gas) are sent through a gas mixture. When the targeted gas is present the targeted gas heats up with every pulse and cools down between pulses creating a sound wave at twice the laser pulsation frequency.

Historically, PAS acoustic waves had been detected by a broadband microphone until the development of an enhancement to PAS referred to as "Quartz Enhanced Photoacoustic Spectroscopy (QEPAS)." QEPAS improves PAS gas detection sensitivity by pulsing the laser light at half the frequency of a high-Q resonant microphone (that is, a quartz tuning fork). Thus QEPAS can distinguish very subtle differences, such as isotopic differences, between reservoir samples which may be indicative of reservoir compartmentalization.

For liquid samples, a membrane can be provided to separate gas from liquid so as to perform isotopic ratio analysis on the gas. It is also possible to assess compartmentalization using analysis of phytane/pristine ratios of liquid crude oil or by using any other distinguishing features such as any unexpected subtle differences in the fluid spectra that are capable of being resolved using a tunable optical filter.

Gravity segregation causes some expected spectral differences in fluids from different depths even when there is no compartmentalization. For example, it is expected that the top of a column of crude oil will be more gas rich than the bottom of the same column of crude oil. However, if the reverse is observed and the bottom of a hydrocarbon column contains a higher percentage of low molecular weight hydrocarbons like methane and ethane than does the top of the column, then there must be a seal between the upper and lower sections of the column and the reservoir is compartmentalized. The same logic applies if one section of a hydrocarbon column has a different isotopic ratio of 13C/12C methane than does another section. Similarly, in a water column, a different isotopic ratio of 18O/17O water indicates that the water column is compartmentalized. For a 2 mm path length of investigation, the dominant liquid hydrocarbon (or C6+) optical absorption peaks are near 1725 nm. The absorption peaks of hydrocarbon gases such as methane, ethane, propane, butane, lie between 1677 nm and 1725 nm. Unexpected variations (variations not expected from gravitational segregation) in relative amounts of methane, ethane, propane, and on can indicate compartmentalization. Also, subtle differences in spectra associated with differences in the amounts of non-hydrocarbon gases can also be evidence of reservoir compartmentalization. For example, H2S gas has a cluster of absorption peaks near 1952 nm and another weaker cluster of peaks near 1578 nm. Similarly, CO2 gas has a cluster of absorption peaks near 2007 nm and another weaker cluster of absorption peaks near 1572 nm. If one section of a hydrocarbon column has substantially more H2S or CO2 gas than does another section of that hydrocarbon column, and these differences cannot be explained by gravitational segregation, then this anomaly is evidence that a seal is separating these two sections and that the reservoir is compartmentalized.

A series of many ratios (typically 5 to 10) of different compounds can be plotted in a "star" pattern (polar coordinates). These ratios could be the percentages of ethane to methane or of phytane to pristane, and so on. Ratios of percentages are preferred over the percentages themselves, because ratios make more reliable oil-type indicators. The distance from the center of the plot to a point represents the value of such a ratio for that point. The angle at which the point is plotted corresponds to which of the compositional ratio is being plotted. Lines can be drawn to connect the plotted points to create polygons. In such plots, each type of oil is represented by a unique polygon. The polygon of one type of oil will not overlay the polygon that corresponds to a different type of oil. There is evidence that the reservoir is compartmentalized when fluids from different parts of the reservoir have different compositional-ratio polygons. Hierarchical cluster analysis can also be used to demonstrate differences among formation hydrocarbons.

"Reservoir compartmentalization" or compartmentalization refers to the presence of fluid flow barriers between two fluid sampling points. Similarly, "reservoir continuity" refers to the absence of vertical fluid flow barriers between two sampling points within a single well (vertical continuity) and/or the absence of lateral continuity barriers between two sampling points in discrete wells (horizontal continuity). For many years, a variety of companies have applied oil geochemistry (oil fingerprinting) or geochemical analysis to reservoir continuity assessment in a diverse range of geological settings (including a wide range of field sizes, structural environments, reservoir lithologies, and oil types). As demonstrated by numerous published and unpublished case studies, petroleum geochemistry provides an effective tool for identifying vertical and lateral fluid flow barriers within oil and gas fields.

Oil geochemistry typically provides a very inexpensive key to interpreting ambiguous geological and/or engineering information. The approach is based on the proposition that oils from discrete reservoirs almost always differ from one another in composition. The technique assesses whether or not two oils are in fluid communication by comparing the relative compositions of each oil. Numerous methods for reservoir characterization based on gas chromatograph (GC) analysis have been devised and are well known in the art. The present invention, however, instead of a GC, uses the PAS or QEPAS to determine the geochemical composition or content of a sample. A processor is provided by the present invention to compare the geochemical analysis of samples to estimate reservoir compartmentalization.

To arrive at an assessment of reservoir compartmentalization, the sample analysis can be integrated with any other available and relevant geological and/or engineering information (such as fault distributions, fault throws, fault shale/sand gouge ratios, lateral changes in reservoir lithology, formation fluid pressure versus depth data, pressure decline curves, oil-water contact depths, etc.).

FIG. 1 is an illustration of a downhole sampling tool 50 used in obtaining a reservoir sample for analysis by the present invention. The present invention gas analysis module containing the QEPAS/PAS and processor can be housed in the downhole tool 50 or alternatively be housed at the surface in controller 1000. In either case the present invention provides a method and apparatus for analysis of samples obtained from various parts of a reservoir. As shown in FIG.

1, a sample is taken at a particular depth at a particular location in the reservoir. Another sample is taken at a different location in the reservoir. Comparison of the two samples based on analysis by the present invention yields an estimate of the likelihood of reservoir compartmentalization.

Figure 2:
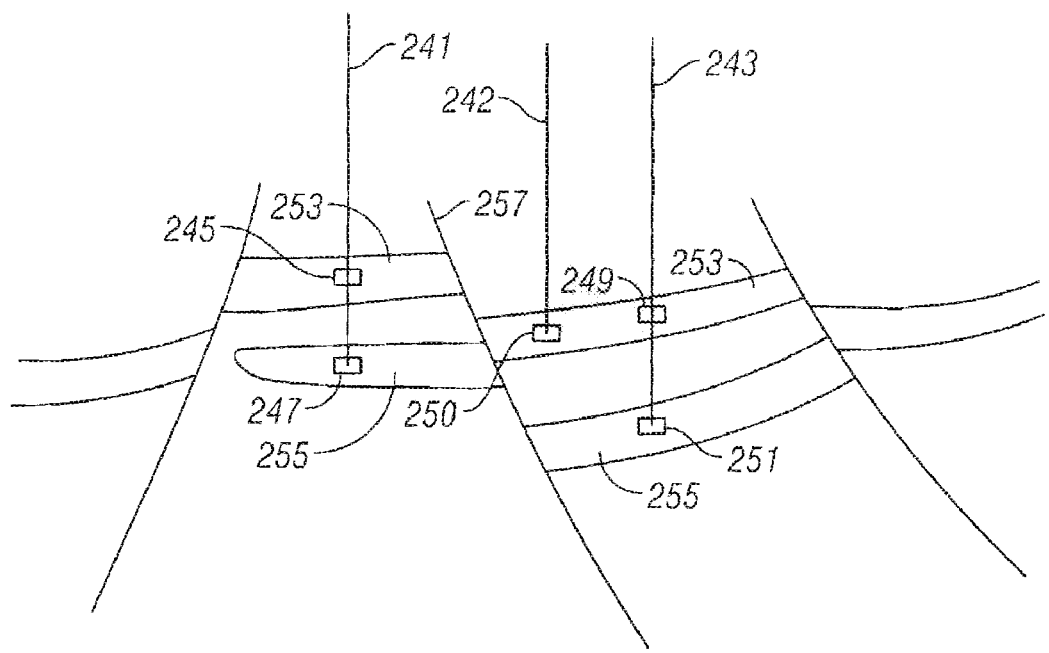
FIG. 2 is an illustration of a downhole tool deployed from wireline used to obtain a sample from a formation within a reservoir.

FIG. 2 illustrates a simplified version of how oil geochemistry composition and finger printing can be used to assess reservoir continuity or conversely, compartmentalization. The composition or fingerprint of five sampling points 245, 247, 249, 250 and 251 in three wells 241, 242 and 243 is shown. Continuity of zone 253 between wells 242 and 243 is suggested by identical geochemical composition or fingerprints from the samples 250 and 249. Compartmentalization (that is, no communication) between zone 253 on the left side of fault line 257 and zone 253 on the right side of fault line 257 is suggested by different geochemical composition and fingerprints between the samples 245 and 250. The geochemical composition data can be integrated with additional geological and engineering data available for the reservoir. Additional engineering data may include but is not limited to pressure gradient data, pressure decline curves, oil/water contact depths, gas oil ratios, permeability, viscosity, mobility, etc.

Returning now to FIG. 1, FIG. 1 illustrates an example of the current invention deployed from a wire line 102 in a borehole 104 drilled in a formation 100. An extensible probe 101 extracts fluid from the formation 100. The extracted formation fluid flow through flow line 105 where the gas analysis chamber 300 of the present invention determines the composition or fingerprint of the formation fluid sample using a PAS or QEPAS. The fluid sample may be a gas or a liquid. The present invention can analyze either a gas or vapor from a liquid. Stablizers 103 hold the tool 50 and extensible probe 101 in place during extraction of a formation fluid sample. The results of the gas analysis performed by the QEPAS/PAS 317 and processor 315 (which are shown in FIG. 4) contained in gas analysis module 300 can be acted on by processor 315 or the sample can be sent to the surface 51 to acted on by the QEPAS/PAS in the gas analysis module 300 at the surface processor and control unit 1000.

Figure 3:
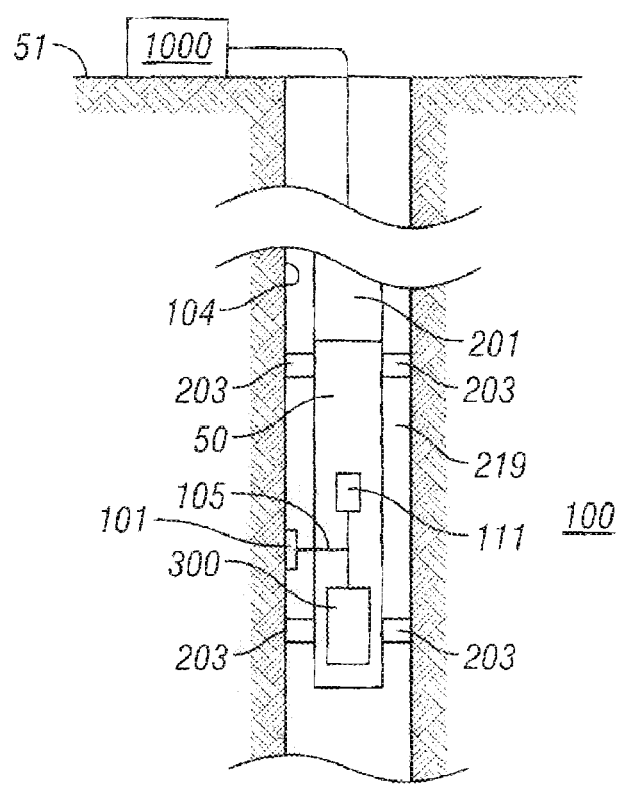
FIG. 3 is an illustration of a downhole tool deployed from a drill string used to obtain a sample from a formation within a reservoir.

Turning now to FIG. 3, another example of the current invention is shown deployed from a drill string 201. Straddle packers 203 hold the tool 50 in place during the entry of fluid through flow path 105 to the gas analysis chamber 300 containing the QEPAS/PAS of the present invention. The fluid can come from the annulus 105 between the tool 50 and the well bore 104 or from the formation 100. Fluid can be routed to the sample tank 111 or back to the well bore annulus 105 as desired based on the results of the density determination performed by the gas analysis module 300 present invention. The results of the QEPAS/PAS analysis are acted on by the processor 106, or the sample can be sent to the surface 51 to be acted on by surface QEPAS/PAS 317 located with processor and control 1000. An additional or optional gas analysis chamber 300 containing the can be duplicated at the surface in processor 1000 for analysis of formation fluid (gas or fluid) samples at surface. Each gas analysis module 300 contains a QEPAS/PAS 317 as shown in FIG. 4.

Figure 4:
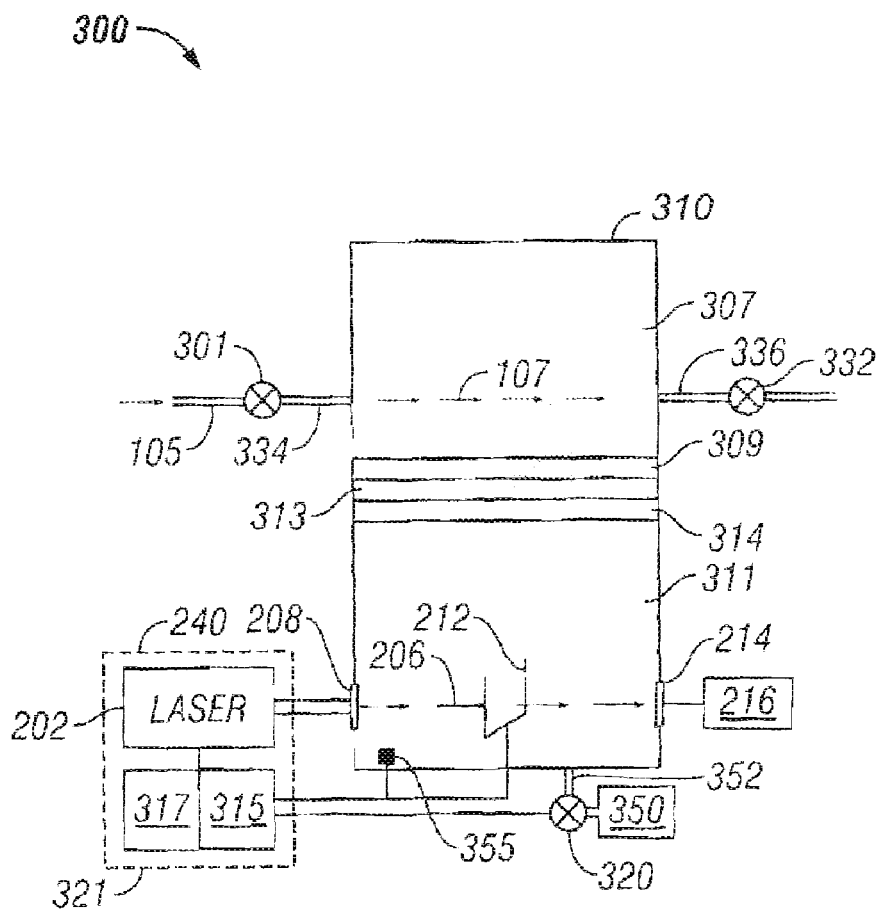
FIG. 4 is an illustration of a gas analysis module containing a Photoacoustic Spectrometer (PAS) and a Quartz Enhanced Photoacoustic Spectrometer (QEPAS) provided by the present invention.

Turning now to FIG. 4, a more detailed schematic of the gas analysis module 300 containing the QEPAS/PAS 317 of the present invention is shown. An QEPAS/PAS 317, optional ion pump 319, semi-permeable membrane 309, fluid containment chamber 307 and processor 315 are shown in schematic form in FIG. 4. A sorption-cooling unit 321 is provided to maintain processor and QEPAS/PAS 317 and control electronics 315 within their operating and/or survival temperature range. The formation fluid containment chamber 307 is separated from the evacuated gas analysis chamber 311 by the semi-permeable membrane 309. Thus, the formation fluid containment chamber 307 is positioned on one side of the semi-permeable membrane 309 and an (optionally evacuated) gas analysis chamber 311 on the other side of the semi-permeable membrane 309. The gases trapped in the formation fluid sample diffuse across the semi-permeable membrane into the (optionally evacuated) gas analysis chamber for analysis.

Figure 5:
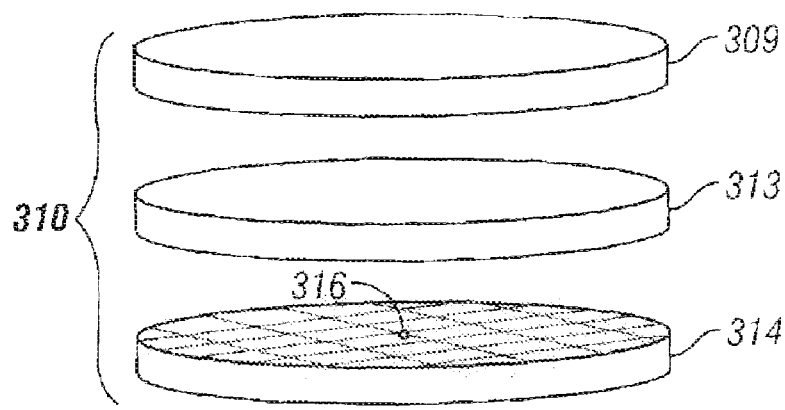
FIG. 5 is an illustration of a semi-permeable membrane provided in an embodiment of the present invention.

Formation fluid is extracted from the formation 100 and enters into the fluid containment chamber 307 via flow line 107 and valve 301. Dissolved gases and liquid vapors diffuse from the formation fluid on the fluid side of the semi-permeable membrane, through the semi-permeable membrane and into the (optionally evacuated) chamber 311. The gas analysis module equipment, QEPAS/PAS 317 and processor/control electronics 315 are located in the (optionally evacuated) gas analysis chamber 311. The gas is exposed to and analyzed by QEPAS/PAS 317 and processor 315. The processor 315 and QEPAS/PAS electronics controls and conducts the QEPAS/PAS analysis. The processor 102 reports the analytical results to the surface via the wire line of other means of downhole communication. The processor 315 can act on the analysis results without reporting the results to the surface. FIG. 5 illustrates the semi-permeable membrane 309, sintered metal filter 313 and metal plate 314 with small hole having scoring of fact of plate between the holes.

The photoacoustic effect was discovered more than one hundred years ago. Photoacoustic commercial gas detection systems became available in the 1960's. Laser photoacoustic spectroscopy (LPAS) is a versatile and highly sensitive absorption-spectroscopic technique. In the simple terms, LPAS involves the absorption of light energy by a molecule and the subsequent detection of a pressure wave caused by heat energy released by the molecule upon return to the ground state. The sensitivity of LPAS arises from the inherently high efficiency of thermal conversion than occurs in most of these light-absorption processes coupled with a similar efficiency in the piezoelectric devices that convert the pressure wave into a voltage pulse. In addition to a laser, an LPAS typically includes a cell to hold the sample, an ultrasonic transducer acoustically coupled to the cell to convert the pressure wave to a voltage pulse and electronics for triggering data collecting and for digitization and storing the output from the transducer.

Photoacoustic spectroscopy (PAS) is an established method of experimental physics. A review of its history and the present state of the art with respect to its use for chemical sensing in the gas phase is well known in the art. A common approach to detecting the acoustic signal generated by the modulated laser radiation in a weakly absorbing gas utilizes an acoustic resonator filled with the gas. QEPAS inverts the common approach to resonant PAS and accumulates the absorbed energy not in the gas but in the sensitive element (i.e., the microphone). A well-suited material for a resonant high-Q microphone is piezoelectric crystal quartz.

Figure 6:
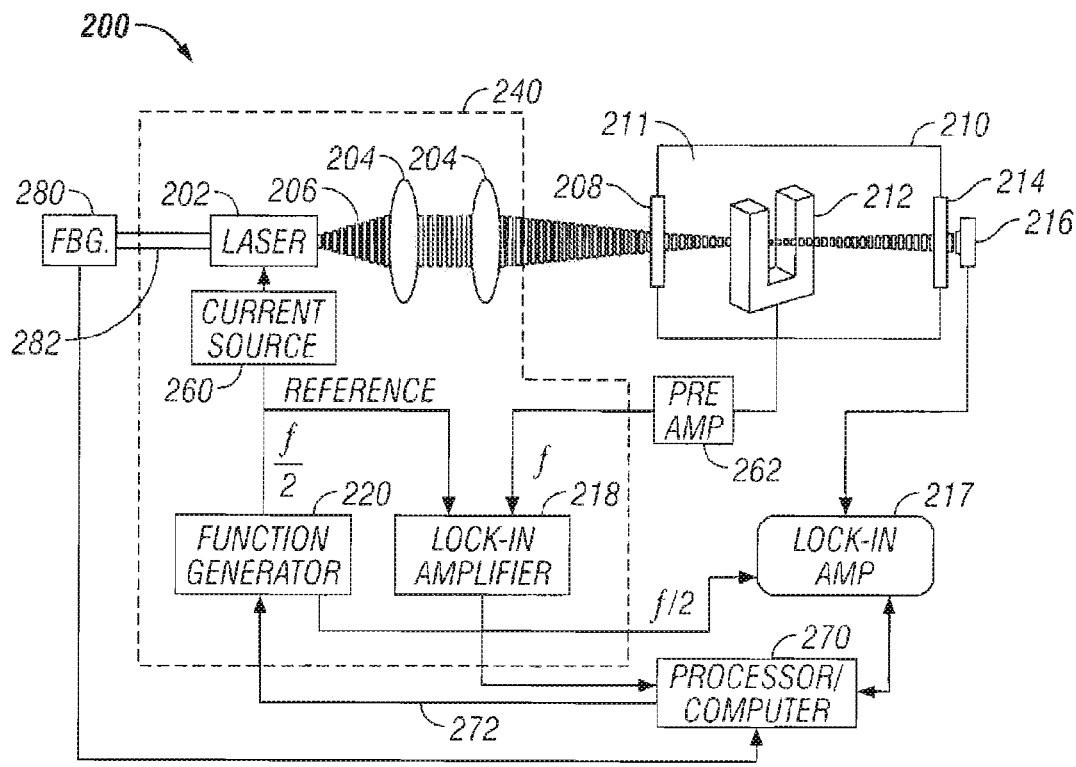
FIG. 6 is an illustration of a Quartz Enhanced Photoacoustic Spectrometer (QEPAS) used in the present invention.

FIG. 6 is an illustration of a QEPAS 317 as provided in the present invention. The QEPAS can be housed in the gas analysis module 300 in the downhole tool 50 or housed in the gas analysis module 300 at the surface in controller 1000 for analysis of samples obtained by the downhole tool. As shown in FIG. 6 in an embodiment of the invention a QEPAS is provided for analyzing a plurality of samples for estimation of compartmentalization of a reservoir. As shown in FIG. 6 a suitable arrangement for a QEPAS comprises a distributed feedback (DFB) diode laser 202 which emits a laser beam 206 through collimation lens 204. The beam enters a window 208 into a 2-5 mm long gas cell 210. The dimensions and structures given herein are for example only and should not be construed as limiting to the scope of the invention. Gas cell 210 contains the gas mixture under investigation 211, for example a mixture of air and methane. To excite a photoacoustic signal the DFB laser is operated at a wavelength of approximately $1.667 \times 10^{-6}$ meters. The tuning fork 212 which interacts with the gas is also located in the gas cell 210. Tuning fork 212 is monitored by lock-in amplifier 218 which also monitors laser frequency feed to laser 202. The laser 202 can be tunable with current or temperature. The temperature can be controlled and current varied or the current controlled and temperature varied. A photodiode 214 can be located after the gas cell 210. The concentration of a particular gas is estimated from the tuning fork response in the QEPAS.

Figure 7:
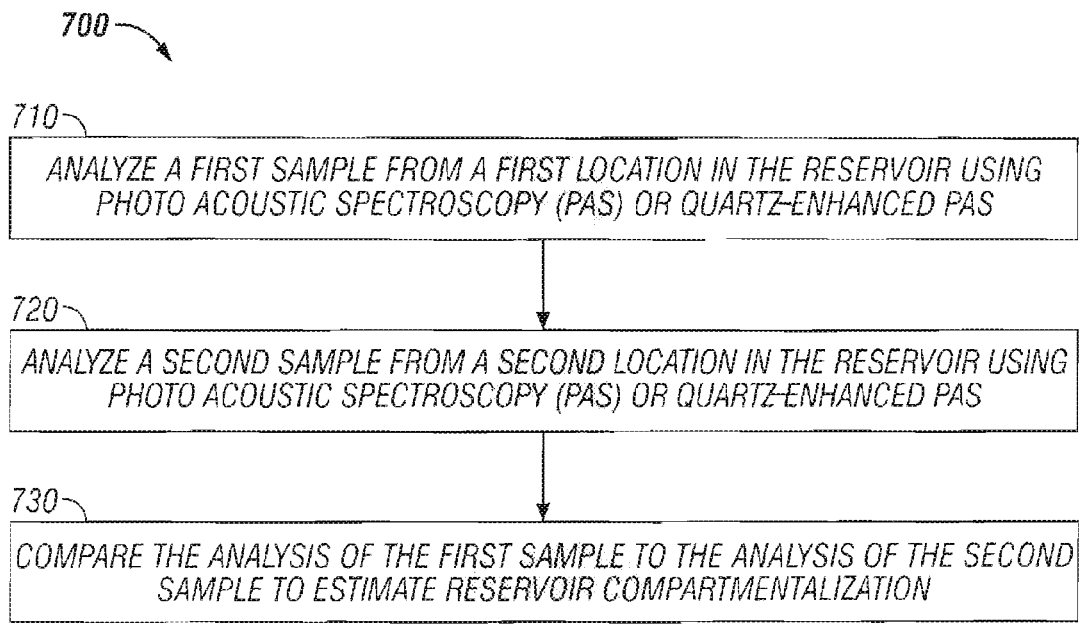
FIG. 7 is an illustration of functions performed in an example of the invention.

Turning now to FIG. 7, an example illustrating some of the functions performed by the present invention is illustrated. In block 710 the present invention analyzes a first sample taken from a first location in the reservoir. In block 720 the present invention analyzes a second sample taken from a second location in the reservoir. In block 730 the present invention estimates the degree of compartmentalization based on a comparison of the analysis for the samples taken from various locations in the reservoir.

The semi-permeable membrane between the fluid and the evacuated chamber allows gases from the fluid to diffuse through the semi-permeable membrane into an evacuated gas analysis chamber. The QEPAS/PAS 317 and processor of the present invention monitors the gases to detect, identify and quantify the gases and distinguish between them. The ion pump optionally removes diffused gases from the evacuated side of the chamber to maintain the vacuum. Suitable semi-permeable membranes, residual gas analyzers and vacuum pumps are commercially available and suitable for use with the present invention are well known in the art. Furthermore, membranes can be specially designed to be selective to the transmission of one gas instead of transmitting many gases as do most silicone membranes.

The analysis can be, but is not limited to, estimation of isotopic ratios, phytane/pristine ratios or any analytical comparison which yields a distinction between samples from a plurality of wells or a plurality of depths in the same well which is indicative of compartmentalization.

While the foregoing disclosure is directed to the exemplary embodiments of the invention, various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

What is claimed is:

1. A method for estimating reservoir compartmentalization comprising:
    analyzing a photoacoustic response from a first sample from a first location in the reservoir;
    analyzing a photoacoustic response from a second sample from a second location in the reservoir; and
    comparing the analysis of the first sample to the analysis of the second sample to estimate reservoir compartmentalization.

2. The method of claim 1, wherein each photoacoustic response comprises a signal from a photoacoustic spectrometer.

3. The method of claim 1, wherein each photoacoustic response comprises a signal from a quartz-enhanced photoacoustic spectrometer.

4. The method of claim 3, wherein analyzing further comprises estimating an isotopic ratio.

5. The method of claim 1, wherein analyzing further comprises estimating sample composition.

6. The method of claim 1, wherein analyzing is performed downhole.

7. The method of claim 1, wherein analyzing further comprises comparing phytane and pristine ratios.

8. The method of claim 1, wherein analyzing further comprises estimating a distinguishing characteristic.

9. An apparatus for estimating reservoir compartmentalization comprising:
    a photoacoustic spectrometer (PAS) configured to analyze a first sample from a first location in the reservoir and analyze a second sample from a second location in the reservoir; and
    a processor configured to compare the analysis of the first sample to the analysis of the—second sample to estimate reservoir compartmentalization.

10. The apparatus of claim 9, wherein the PAS further comprises a quartz-enhanced PAS.

11. The apparatus of claim 9, wherein the processor is further configured to estimate compartmentalization using isotopic ratios for the samples.

12. The apparatus of claim 11, wherein the isotopic ratios further comprise at least one of the set consisting of isotopic ratios of carbon ($^{13}C/^{12}C$) and isotopic ratios of oxygen ($^{17}O/^{18}O$).

13. The apparatus of claim 9, wherein the processor is further configured to estimate sample composition.

14. The apparatus of claim 9, wherein the analysis is performed downhole.

15. The apparatus of claim 9, wherein the analysis further comprises comparing phytane and pristine ratios.

16. The apparatus of claim 9, wherein the analysis further comprises a comparison of a distinguishing characteristic of the samples.

17. An apparatus for estimating reservoir compartmentalization, comprising:
    a downhole tool configured to obtain samples from the reservoir;
    a photoacoustic spectrometer (PAS) configured to analyze a first sample from a first location in the reservoir and analyze a second sample from a second location in the reservoir; and
    a processor configured to compare the analysis of the first sample to the analysis of the second sample to estimate reservoir compartmentalization.

18. The apparatus of claim 17, wherein the PAS further comprises a quartz enhanced PAS.

19. The apparatus of claim 17, wherein the processor is further configured to estimate compartmentalization from a comparison of isotopic ratios from the first and second samples.

20. The apparatus of claim 17, wherein the processor is further configured to compare a distinguishing characteristic of the first and second samples to estimate reservoir compartmentalization.

* * * * *